US010143506B2

(12) United States Patent
Dreyfuss et al.

(10) Patent No.: US 10,143,506 B2
(45) Date of Patent: Dec. 4, 2018

(54) METHOD AND SYSTEM FOR PROVIDING A SUTURE WRAP CERCLAGE

(71) Applicant: ARTHREX, INC., Naples, FL (US)

(72) Inventors: Peter Dreyfuss, Naples, FL (US); Andrew Christian Petry, Naples, FL (US); Donald K. Shuler, Naples, FL (US); Brian S. Cohen, Dublin, OH (US); Reuben Gobezie, Chagrin Falls, OH (US); Peter J. Millett, Edwards, CO (US); Laurence D. Higgins, Brookline, MA (US); Paul C. Brady, Knoxville, TN (US)

(73) Assignee: ARTHREX, INC., Naples, FL (US)

( * ) Notice: Subject to any disclaimer, the term of this patent is extended or adjusted under 35 U.S.C. 154(b) by 220 days.

(21) Appl. No.: 15/073,217

(22) Filed: Mar. 17, 2016

(65) Prior Publication Data

US 2017/0265917 A1    Sep. 21, 2017

(51) Int. Cl.
*A61B 17/82* (2006.01)
*A61B 17/04* (2006.01)
*A61B 17/06* (2006.01)

(52) U.S. Cl.
CPC .......... *A61B 17/82* (2013.01); *A61B 17/0401* (2013.01); *A61B 17/0469* (2013.01); *A61B 17/06166* (2013.01); *A61B 2017/044* (2013.01); *A61B 2017/0477* (2013.01); *A61B 2017/0496* (2013.01); *A61B 2017/06176* (2013.01)

(58) Field of Classification Search
CPC ............ A61B 17/0475; A61B 17/0477; A61B 17/048; A61B 17/1796; A61B 17/7053; A61B 17/82–17/826; A61B 17/842; A61B 17/8861; B65B 11/00–11/585
USPC .................................. 289/1.2–18.1
See application file for complete search history.

(56) References Cited

U.S. PATENT DOCUMENTS

| 3,111,945 A | 11/1963 | Von Solbrig |
| 3,469,573 A | 9/1969 | Florio |
| 4,008,912 A * | 2/1977 | Kotov ................... B65D 63/12 289/1.2 |
| 4,119,091 A | 10/1978 | Partridge |
| 4,146,022 A | 3/1979 | Johnson et al. |
| 4,606,335 A | 8/1986 | Wedeen |
| 4,643,178 A | 2/1987 | Nastari et al. |
| 4,667,662 A | 5/1987 | Titone et al. |
| 5,012,818 A | 5/1991 | Joishy |
| 5,190,545 A | 3/1993 | Corsi |

(Continued)

FOREIGN PATENT DOCUMENTS

WO    2015009808 A1    1/2015

OTHER PUBLICATIONS

Y.M. Por, M.J. Lavin, "Techniques of intraocular lens suspension in the absence of capsular/zonular support", Survey of Ophthalmology, vol. 50, nr. 5, Sep.-Oct. 2005.

(Continued)

*Primary Examiner* — Matthew Lawson
(74) *Attorney, Agent, or Firm* — Carlson, Gaskey & Olds, P.C.

(57) ABSTRACT

A method for providing a fractured bone with a bone cerclage according to an exemplary aspect of the present disclosure includes, among other things, wrapping a folded piece of suture around a bone at least once, and securing the suture to the bone.

17 Claims, 8 Drawing Sheets

(56) References Cited

U.S. PATENT DOCUMENTS

| | | | |
|---|---|---|---|
| 5,199,135 A * | 4/1993 | Gold | B65D 63/18 24/16 R |
| 5,250,053 A | 10/1993 | Snyder et al. | |
| 5,318,566 A | 6/1994 | Miller | |
| 5,415,658 A | 5/1995 | Kilpela et al. | |
| 5,454,821 A * | 10/1995 | Harm | A61B 17/0469 289/17 |
| 5,462,542 A | 10/1995 | Alesi | |
| 5,501,688 A * | 3/1996 | Whiteside | A61B 17/8861 140/119 |
| 5,540,703 A | 7/1996 | Barker, Jr. | |
| 5,573,286 A | 11/1996 | Rogozinski | |
| 5,573,542 A | 11/1996 | Stevens et al. | |
| 5,628,756 A | 5/1997 | Barker, Jr. | |
| 5,772,663 A | 6/1998 | Whiteside et al. | |
| 5,788,697 A | 8/1998 | Kilpela | |
| 5,830,234 A | 11/1998 | Wojciechowicz et al. | |
| 5,851,209 A | 12/1998 | Kummer | |
| 5,908,421 A * | 6/1999 | Beger | A61B 17/82 606/151 |
| 6,093,190 A | 7/2000 | Mattchen | |
| 6,302,889 B1 | 10/2001 | Keller | |
| 6,368,326 B1 | 4/2002 | Dakin et al. | |
| 6,610,071 B1 | 8/2003 | Cohn et al. | |
| 6,716,234 B2 | 4/2004 | Grafton et al. | |
| 6,793,595 B1 * | 9/2004 | Monnet | A63B 63/004 473/478 |
| 7,207,090 B2 | 4/2007 | Mattchen | |
| 7,207,993 B1 | 4/2007 | Baldwin | |
| 7,326,222 B2 | 2/2008 | Dreyfuss | |
| 8,162,997 B2 | 4/2012 | Struhl | |
| 8,216,221 B2 * | 7/2012 | Ibrahim | A61B 18/1492 606/34 |
| 8,231,626 B2 | 7/2012 | Hulliger | |
| 8,298,247 B2 | 10/2012 | Sterrett et al. | |
| 8,337,534 B2 | 12/2012 | Celli | |
| 8,460,295 B2 | 6/2013 | McClellan et al. | |
| 8,574,235 B2 | 11/2013 | Stone | |
| 8,672,969 B2 | 3/2014 | Stone | |
| 8,984,720 B2 | 3/2015 | Gephart | |
| 2003/0208210 A1 * | 11/2003 | Dreyfuss | A61B 17/0469 606/144 |
| 2005/0033365 A1 * | 2/2005 | Courage | A61B 17/0485 606/232 |
| 2005/0273983 A1 * | 12/2005 | Mattchen | A61B 17/82 24/136 R |
| 2009/0306668 A1 | 12/2009 | Dell'Oca | |
| 2010/0211075 A1 * | 8/2010 | Stone | A61B 17/0401 606/70 |
| 2010/0249853 A1 | 9/2010 | Celli | |
| 2012/0109129 A1 * | 5/2012 | Bernstein | A61B 17/823 606/74 |
| 2013/0018375 A1 | 1/2013 | Dell'Oca | |
| 2013/0096612 A1 | 4/2013 | Zajac et al. | |
| 2013/0239974 A1 | 9/2013 | O'Brien et al. | |
| 2014/0249530 A1 | 9/2014 | Babikian | |
| 2014/0257377 A1 | 9/2014 | Akutsu et al. | |
| 2015/0127003 A1 | 5/2015 | Songer | |
| 2015/0359577 A1 * | 12/2015 | Akatsu | A61B 17/82 606/74 |
| 2016/0183991 A1 | 6/2016 | Pratt | |

OTHER PUBLICATIONS

International Preliminary Report on Patentability for International Application No. PCT/US2017/014924 dated Sep. 27, 2018.

* cited by examiner

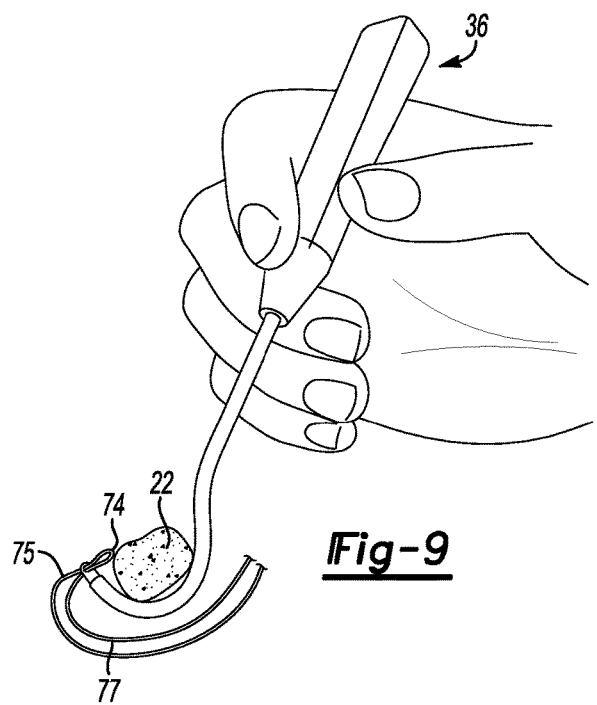
*Fig-9*
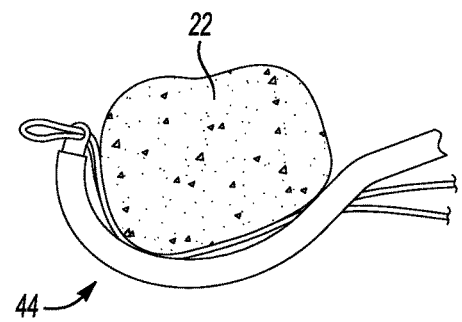
*Fig-10*
*Fig-11*
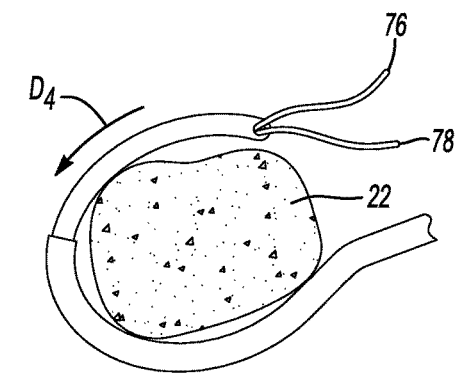
*Fig-12*
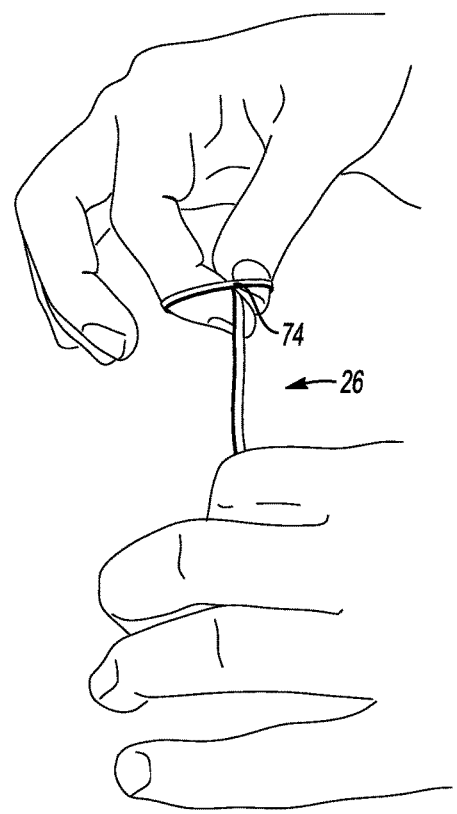
*Fig-13*

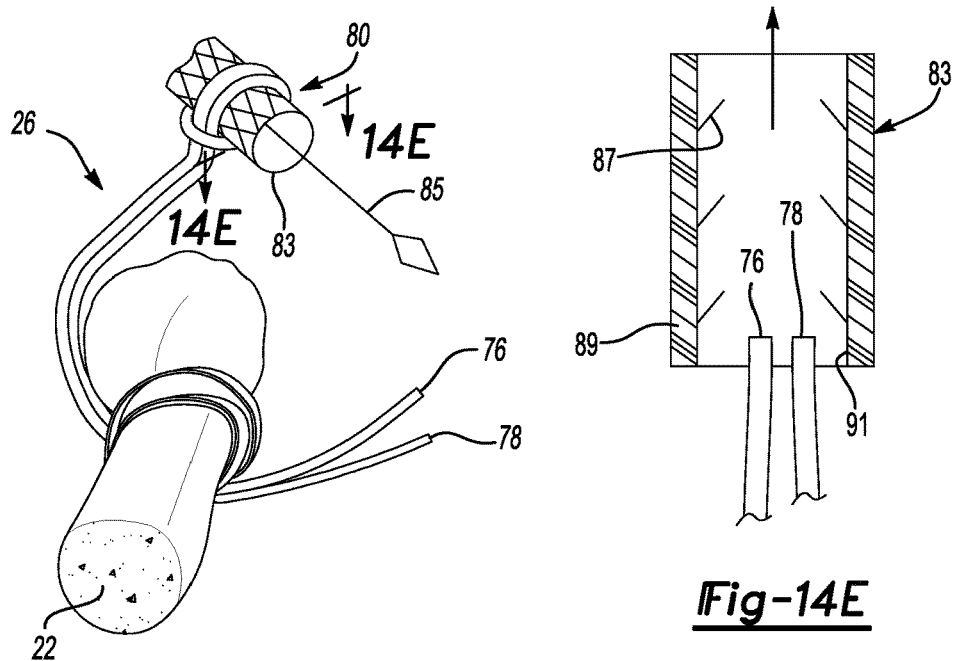
Fig-14D
Fig-14E
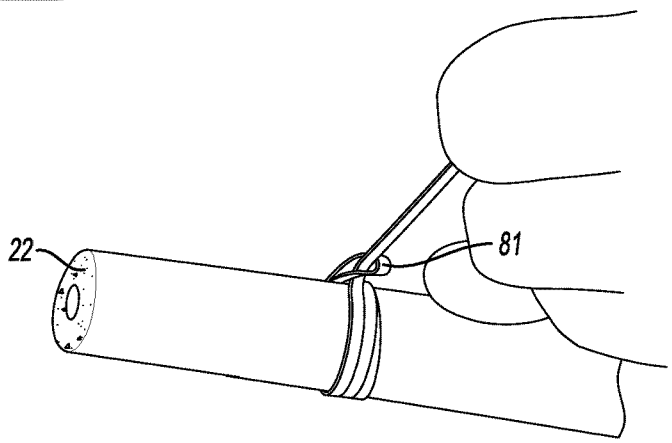
Fig-15
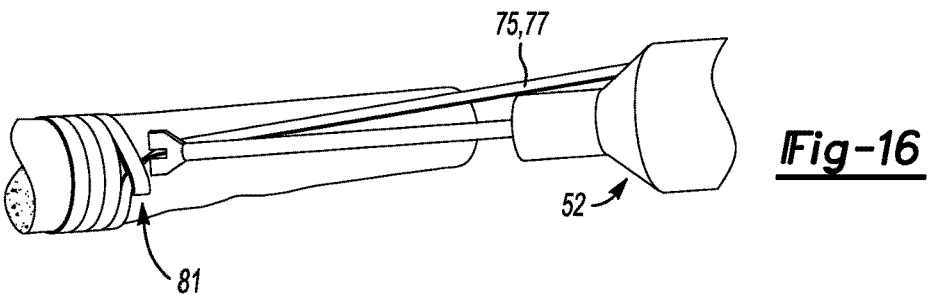
Fig-16

METHOD AND SYSTEM FOR PROVIDING A SUTURE WRAP CERCLAGE

BACKGROUND

This disclosure relates to a method and system for providing a bone cerclage.

Cerclages are used to maintain the relative position of fractured bone fragments to promote healing. While cerclages can be used relative to any fractured bone, they are commonly used to promote healing of femoral fractures. Femoral fractures are sometimes caused, for example, by traumatic injuries or as the result of an orthopedic procedure such as a hip replacement. A cerclage is used to fix fractured bone fragments relative to one another, which, again, promotes healing.

Known cerclages include materials such as cable (i.e., wire) or fabric, and are provided by wrapping the cable or fabric around a fractured bone a single time. After wrapping, the cable or fabric is then locked into place relative to the bone, such as with a plug or clip.

SUMMARY

This disclosure details a method and system for providing a bone cerclage. The disclosed method includes wrapping a piece of material around a bone, and securing that material relative to the bone. The wrapped material provides a bone cerclage, which maintains the relative position of fractured bone fragments to promote healing.

A method for providing a fractured bone with a bone cerclage according to an exemplary aspect of the present disclosure includes, among other things, wrapping a folded piece of suture around a bone at least once, and securing the suture to the bone.

In a further non-limiting embodiment of the foregoing method, the suture is wrapped around the bone at least twice.

In a further non-limiting embodiment of either of the foregoing methods, the wrapping step comprises wrapping the suture around the bone a first time by moving a folded end around the bone in a first direction, and wrapping the suture around the bone a second time by moving first and second free ends of the suture around the bone in a second direction opposite the first direction.

In a further non-limiting embodiment of any of the foregoing methods, the folded end is pushed around the bone using a suture passer.

In a further non-limiting embodiment of any of the foregoing methods, the first and second free ends are pulled around the bone by the suture passer after the folded end is pushed around the bone.

In a further non-limiting embodiment of any of the foregoing methods, the securing step includes securing the suture to the bone by tying a knot.

In a further non-limiting embodiment of any of the foregoing methods, the securing step includes providing a sliding knot between the folded end and the first and second free ends.

In a further non-limiting embodiment of any of the foregoing methods, the sliding knot is partially pre-tied and includes an eyelet provided within a sheath.

In a further non-limiting embodiment of any of the foregoing methods, the sheath includes at least one barb configured to resist removal of suture from the sheath.

In a further non-limiting embodiment of any of the foregoing methods, the wrapped suture is tensioned to tighten it relative to the bone.

In a further non-limiting embodiment of any of the foregoing methods, the tensioning step includes using a tensioner to pull the first and second ends relative to the sliding knot to tighten the wrapped suture.

In a further non-limiting embodiment of any of the foregoing methods, the securing step includes securing the suture to the bone without tying any knots.

In a further non-limiting embodiment of any of the foregoing methods, the securing step includes anchoring the suture to the bone using a knotless anchor.

In a further non-limiting embodiment of any of the foregoing methods, a portion of the suture providing a first wrap around the bone is secured to the bone by a suture-retaining feature formed in the bone.

In a further non-limiting embodiment of any of the foregoing methods, the suture is a self-cinching suture including at least one splice, and the securing step includes pulling a portion of the self-cinching suture through the at least one splice to tension to the suture to the bone.

In a further non-limiting embodiment of any of the foregoing methods, a bone screw maintains a position of the suture as the suture is wrapped around the bone, and the step of securing the suture to the bone includes tightening the suture against the bone using the bone screw.

In a further non-limiting embodiment of any of the foregoing methods, the suture passes through an eyelet of a bone plate as the suture is wrapped around the bone.

A system for providing a bone cerclage according to an exemplary aspect of the present disclosure includes, among other things, a suture and a suture passer. The suture passer is configured to wrap the suture around a bone a first time by moving a first portion of the suture around the bone in a first direction. The suture passer is further configured to wrap the suture around the bone a second time by moving a second portion of the suture around the bone in a second direction opposite the first direction.

In a further non-limiting embodiment of either of the foregoing systems, the suture passer includes a handle, a cannula, and a moveable suture carrier. The moveable suture carrier has an eyelet for receiving the suture and being moveable relative to the cannula.

A suture passer according to an exemplary aspect of the present disclosure includes, among other things, a handle, a cannula projecting distally from the handle. The cannula includes a portion that is curved to conform to a bone anatomy. The suture passer further includes a moveable suture carrier at least partially received within the cannula. The moveable suture carrier is moveable relative to the cannula and has an eyelet for receiving suture.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

BRIEF DESCRIPTION OF THE DRAWINGS

The drawings can be briefly described as follows:

FIG. 7A illustrates a piece of suture.

FIG. 7B illustrates the piece of suture folded lengthwise.

FIG. 8 illustrates an example method step of inserting a folded end of suture into an eyelet of a suture passer.

FIG. 9 illustrates an example method step of maneuvering the suture passer around a bone.

FIG. 10 illustrates the suture passer around the bone and in a first position.

FIG. 11 illustrates the suture passer around the bone and in a second position.

FIG. 12 illustrates an example method step of inserting free ends of suture into an eyelet of the suture passer.

FIG. 13 illustrates an example method step of tying a sliding knot, and in particular illustrates an eyelet being formed by the folded end of suture.

FIG. 14D illustrates a partially pre-tied knot including an eyelet provided within a sheath.

FIG. 14E is a cross-sectional view of the sheath of FIG. 14D.

FIG. 15 illustrates an example method step of tying a sliding knot, and in particular illustrates tightening the sliding knot relative to the bone.

FIG. 16 illustrates an example method step of tensioning the sliding knot using a tensioner.

DETAILED DESCRIPTION

This disclosure details a method and system for providing a bone cerclage. The disclosed method includes wrapping a piece of material around a bone, and securing that material relative to the bone. The wrapped material provides a bone cerclage, which maintains the relative position of fractured bone fragments to promote healing.

Figure 1:
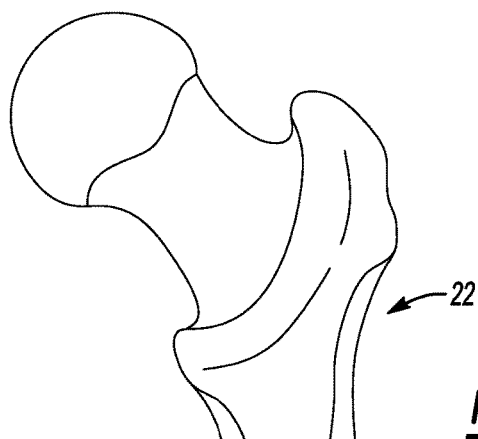
FIG. 1 illustrates a fractured bone provided with a suture wrap cerclage.

This disclosure includes several embodiments of a bone cerclage where the material providing the cerclage is suture. FIG. 1 illustrates a non-limiting example of a suture wrap cerclage 20 provided relative to a bone 22 with a fracture 24.

In this example, the bone 22 is a femur. Femurs can fracture, for example, from a traumatic injury or as the result an orthopedic procedure, such as a hip replacement. The suture wrap cerclage 20 fixes the fractured fragments of the bone 22 relative to one another, which promotes healing. While specific reference is made to femurs, it should be understood that this disclosure is not limited to femoral fractures, and extends to other bones (such as the humerus).

Again, this disclosure includes several embodiments that relate to a method and system for providing a suture wrap cerclage. In one non-limiting example of the disclosed method, a surgeon, for example, may make use of a collection of components, referred to herein as a "system." Among other things, an example system includes suture 26, which forms the suture wrap cerclage 20.

Figure 2:
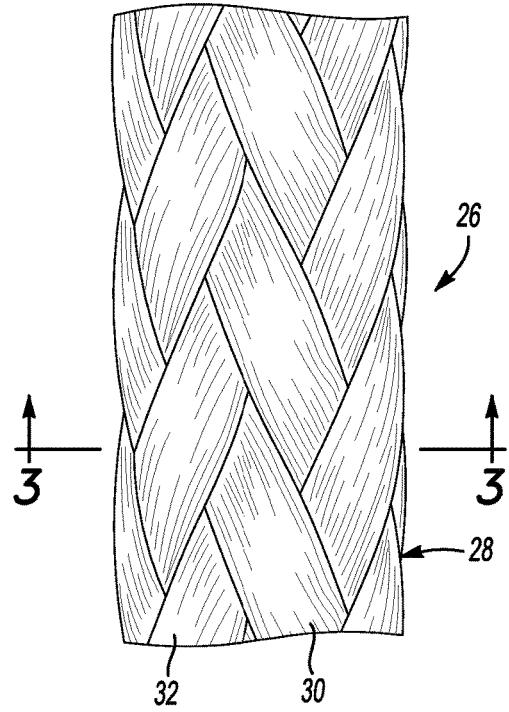
FIG. 2 is an external view of an example suture.
Figure 3:
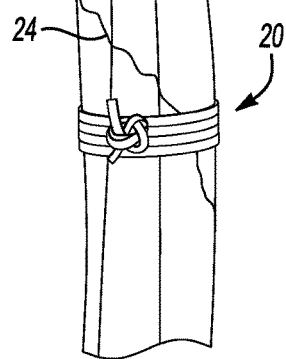
FIG. 3 is a cross-sectional view of the example suture, taken along line 3-3 of FIG. 2.

An external view of an example suture 26 is illustrated in FIG. 2, and a cross-section is shown in FIG. 3. In this non-limiting example, the suture 26 is a high strength braided suture, such as Arthrex, Inc.'s FiberTape™.

In general, the suture 26 includes a multifilament cover 28 formed of a plurality of braided fibers of ultrahigh molecular weight polyethylene (UHMWPE) 30 and fibers of polyester 32. The cover 28 surrounds a core 34 formed of twisted fibers of ultrahigh molecular weight polyethylene (UHMWPE). While one example type of suture 26 is shown and described, it should be understood that other types of suture come within the scope of this disclosure.

Figure 4:
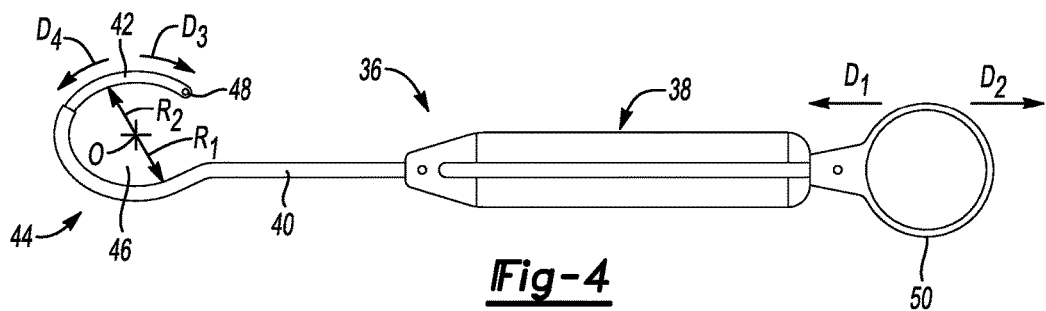
FIG. 4 illustrates an example suture passer.

In addition to suture, the example system also includes a suture passer, such as the suture passer 36 illustrated in FIG. 4. As shown in FIG. 4, the suture passer 36 includes a handle 38, a cannula 40 extending distally from the handle 38, and a moveable suture carrier 42. In this example, the cannula 40 is substantially straight relative to the handle 38, and is curved at a distal end 44 to follow an expected contour of a bone (such as the bone 22 of FIG. 1). The distal end 44 follows a constant radius $R_1$ having an origin O in an expected bone location 46.

The moveable suture carrier 42 has an eyelet 48 for receiving suture, and is moveable relative to the cannula 40 in response to a corresponding movement of an actuation member 50 adjacent a proximal end of the handle 38. The suture carrier 42 has a curve adjacent the distal end 44 substantially following a constant radius $R_2$, which corresponds to the expected contour of a bone, and is substantially the same as the radius $R_1$. Further, in this example, the actuation member 50 is formed as a circular ring. It should be understood that the actuation member 50 could have other configurations.

In one example, the suture carrier 42 is integrally formed with the actuation member 50. In that case, the suture carrier-actuation member structure would be formed of a semi-rigid material, such as a relatively high strength plastic material, to allow the structure to pass through the cannula 40. In other examples, the suture carrier 42 and actuation member 50 may be formed separately from one another, and, in that case, can be formed of metallic material. This disclosure is not limited to any particular material type, however.

The actuation member 50 is slidable relative to the handle 38 in a distal direction $D_1$ and a proximal direction $D_2$. In response to movement of the actuation member 50 in the distal direction $D_1$, the suture carrier 42 is moveable in a direction $D_3$ away from a distal end 44 of the cannula 40. Likewise, in response to movement of the actuation member 50 in the proximal direction $D_2$, the suture carrier moves in a direction $D_4$ toward the distal end 44 of the cannula 40.

Movement of the suture carrier 42 increases the ease of passing suture around a bone.

Figure 5:
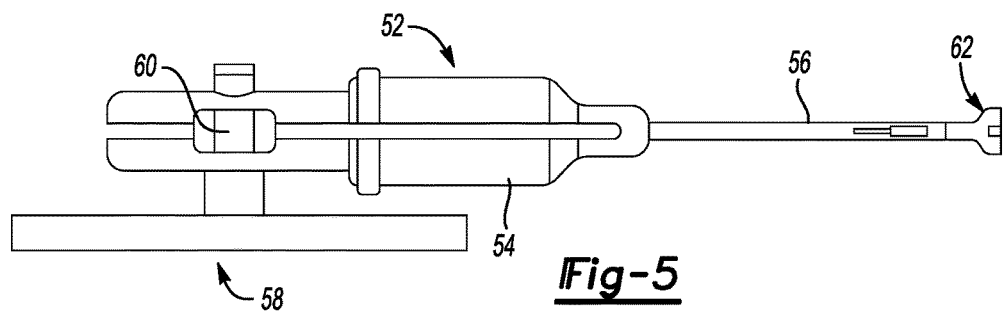
FIG. 5 illustrates an example tensioner.

The example system may further include a suture tensioner, such as the suture tensioner 52 illustrated in FIG. 5. A suture tensioner is a device that allows a surgeon, for example, to tension suture to an appropriate level, such as Arthrex's AR-1529 Suture Tensioner and Tensiometer.

In general, as illustrated in FIG. 5, the suture tensioner 52 includes a handle 54, a shaft 56, and an adjustment wheel 58. As will be further explained below, a free end of suture can be provided around a spool 60 connected to the adjustment wheel 58. The adjustment wheel 58 is then rotated to tension the suture. The suture tensioner 52 may optionally be used in combination with a spreader 62 (shown somewhat schematically), configured to keep adjacent free ends of suture spaced-apart from one another as the spool rotates. The suture tensioner 52 is not required in all examples, but its use may increase the overall tightness of the suture wrap cerclage 20 relative to a hand-tensioned cerclage. Its use may further increase efficiency and repeatability relative to hand-tensioning.

Figure 6:
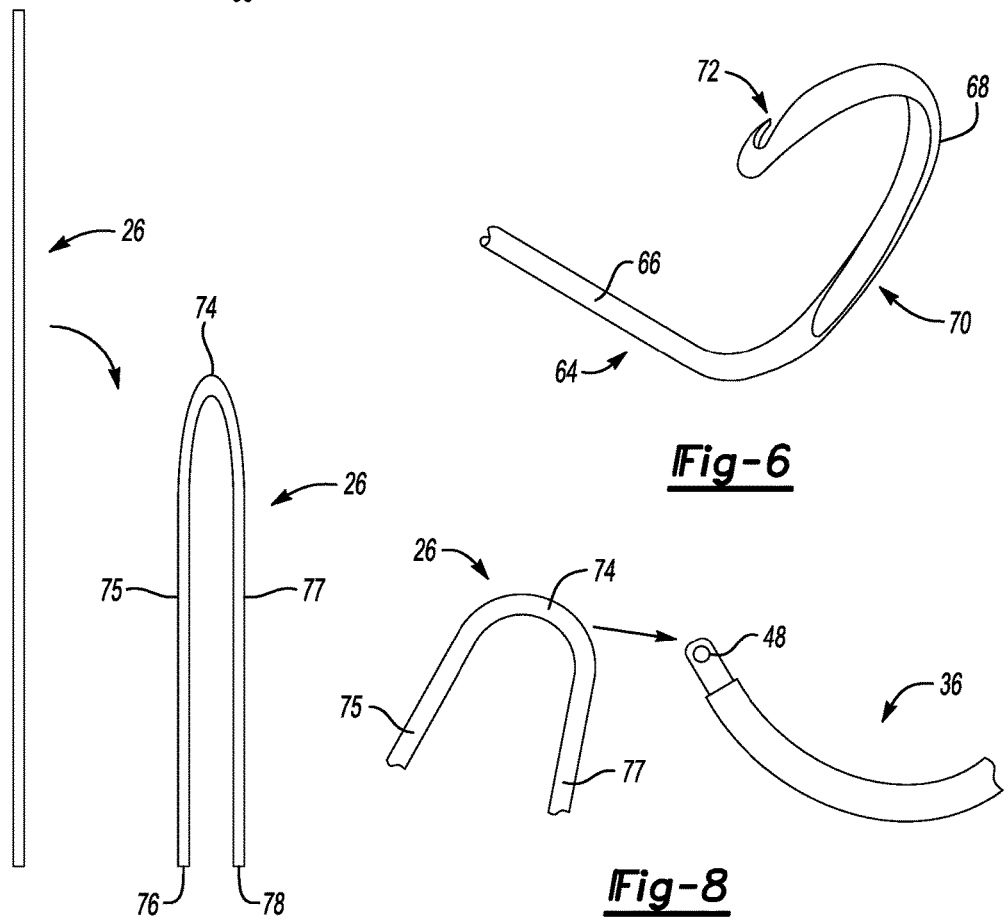
FIG. 6 illustrates another example suture passer.

While FIG. 4 illustrates one example suture passer 36, other suture passers come within the scope of this disclosure. For instance, FIG. 6 illustrates a non-cannulated suture passer 64 having a substantially straight portion 66 and a curved portion 68 at a distal end 70. At an end of the curved portion 68, the suture passer 64 includes a suture retaining member 72, which in the FIG. 6 example is a notch. While a notch is shown, it should be understood that the suture passer 64 could be provided with another type of suture retainer, such as an eyelet.

A first example method of providing the suture wrap cerclage 20 will now be explained with reference to FIGS. 7A-16. In general, the method includes wrapping a suture around a bone at least twice, and then securing the suture to the bone. The method will be explained relative to the suture 26, suture passer 36, and the tensioner 52. While specific reference is made to these devices, it should be understood that other devices may be used.

Initially, a piece of suture 26 (FIG. 7A) is folded substantially in half (FIG. 7B) about its length to provide a folded end 74, and first and second lengths 75, 77 between the folded end 74 and respective first and second free ends 76, 78. The folded end 74 is then placed in the eyelet 48 of the suture passer 36, as shown in FIG. 8.

With the folded end 74 placed in the eyelet 48, the distal end 44 of the cannula 40 is maneuvered around a bone 22, as illustrated in FIG. 9, to push the folded end 74 around the bone 22. As the folded end 74 is moved around the bone 22, the free ends 76, 78 are retained in their original position. In the position of FIG. 10, the suture folded end 74 is only partially wrapped around the bone 22. In order to fully wrap the suture 26 around the bone 22, the suture carrier 42 is moved in the direction $D_3$ by distal movement of the actuation member 50 in the direction $D_1$ (see FIG. 1). In FIG. 11, the folded end 74 has been moved to a position where a surgeon, for example, can grasp the folded end, completing the first wrap around the bone 22. Again, in this example, the suture 26 is folded. Thus, the first wrap includes a wrapping of both the first and second lengths 75, 77 of suture.

Next, the surgeon maintains the position of the folded end 74, which has been wrapped around the bone, and feeds the two free ends 76, 78, which are still in their original position, through the eyelet 48, as illustrated in FIG. 12. Then, the suture carrier 42 is moved in the direction $D_4$ to draw the free ends 76, 78 of suture back toward the cannula 40. Then, the suture passer 36 is maneuvered to pull the free ends 76, 78 back around the bone 22.

By wrapping the folded end 74 around the bone in a first direction while maintaining the position of the free ends 76, 78, and then wrapping the free ends 76, 78 about the bone in a second, opposite direction while maintaining the position of the folded end 74, the result is a single piece of folded suture that has been wrapped around the bone twice. Further, because the suture 26 is folded, the above technique provides a cerclage having the effective width of the four pieces of suture, which increases the coverage and effectiveness of the suture wrap cerclage 20.

Further, the above technique only requires a suture passer to be maneuvered around the bone and removed once, which reduces the time required to wrap the suture and reduces risk of further injury to adjacent soft tissue during surgery. While the suture 26 is wrapped around the bone 22 twice in the above example, the suture 26 could be wrapped only once or additional times depending on the severity of the fracture, for example.

Figure 14:
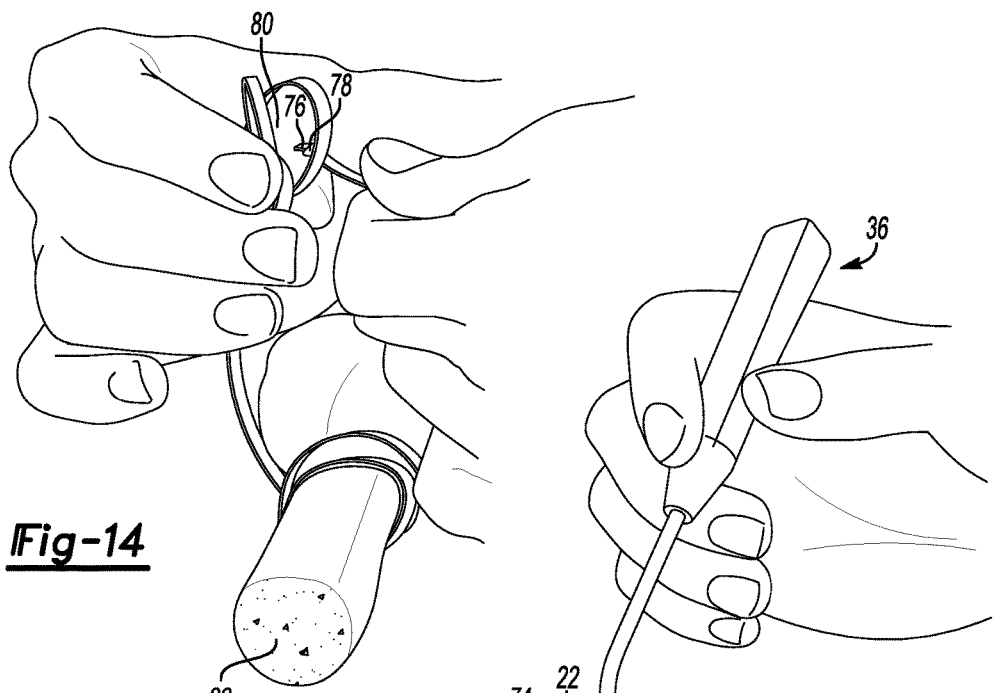
FIG. 14 illustrates an example method step of tying a sliding knot, and in particular illustrates the free ends of suture being placed through the eyelet.
Figure 14A:
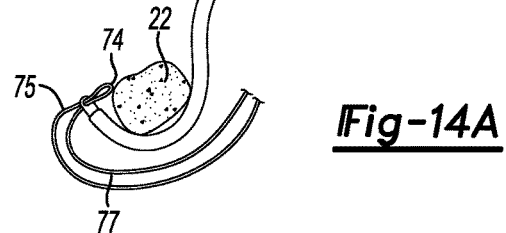
FIG. 14A illustrates an example method step of maneuvering the suture passer around bone.
Figure 14B:
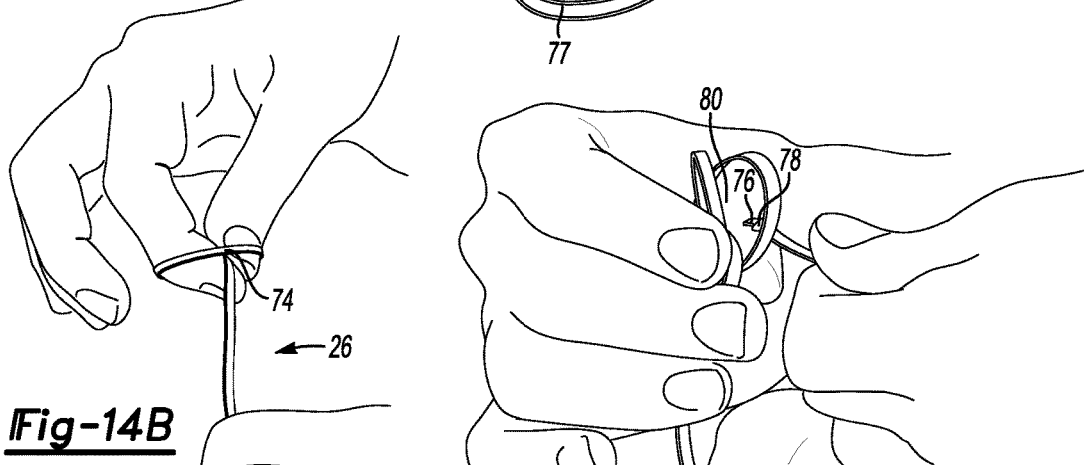
FIG. 14B illustrates an example method step of tying a sliding knot, and in particular illustrates an eyelet being formed by the folded suture.
Figure 14C:
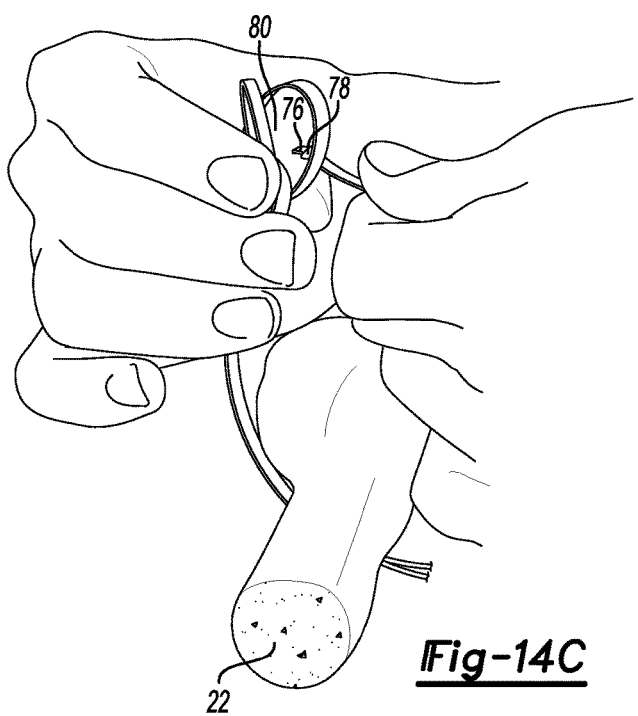
FIG. 14C illustrates an example method step of tying a sliding knot relative to suture that has been wrapped around bone only once.

Once wrapped around the bone 22, the suture 26 is then secured to the bone. In one example, a sliding knot is provided between the folded end 74 and the first and second free ends 76, 78. To provide the sliding knot, the folded end 74 is folded over an adjacent portion of the lengths 75, 77 (FIG. 13) to provide an eyelet 80 (FIG. 14). FIGS. 14A-14C illustrate an example in which the suture 26 is wrapped around the bone 22 only once. In FIG. 14A, for example, the folded end 74 is passed around the bone as substantially described relative to FIGS. 9-11. In FIG. 14B, the folded end 74 is then folded over an adjacent portion of the lengths to provide an eyelet 80 (FIG. 14C). Regardless of the number of times the suture 26 is wrapped around the bone 22, the first and second free ends 76, 78 are then fed through the eyelet 80 to provide a sliding knot 81 (FIG. 15), which is tightened by hand against the bone 22.

Alternatively, the sliding knot 81 could be partially pre-tied. In particular, the eyelet 80 could be provided within a sheath 83, as illustrated in FIG. 14D. In this example, a sheath 83 of suture material is connected adjacent the folded end 74 prior to surgery such that a surgeon, for example, does not have to fold the suture and form the eyelet 80 during surgery. The sheath 83 in this example is substantially cylindrical, and is formed of a mesh-like suture material. In one example, suture is used to stitch the sheath 83 to the lengths 75, 77 to maintain the eyelet 80. A suture shuttle 85 may be used to pass the free ends 76, 78 through the sheath 83. Once suture is passed through the sheath 83, the sliding knot 81 can be tightened as substantially shown in FIG. 15.

Further, as illustrated in FIG. 14E, the sheath 83 may include one or more barbs 87 extending inwardly from a wall 89 of the sheath 83. The barbs 87 in this example are provided by a suture material and are inclined away from a sheath inlet 91. The barbs 87 are configured to engage the suture passing through the sheath 83. For example, when the sliding knot 81 is tightened, the sheath 83 essentially collapses against the suture within the sheath. In this way, the barbs 87 are configured to allow suture to pass into through the sheath inlet 91, while resisting removal of the suture from the sheath 83. The barbs 87 are optional and are not required in all examples.

The sliding knot 81 is then tensioned. In this example, tension is applied by wrapping the first and second free ends 76, 78 around the spool 60 of the suture tensioner 52, and rotating the adjustment wheel 58 until the desired tension is reached, as generally illustrated in FIG. 16. Finally, at least one knot is tied between the first and second free ends 76, 78 to hold the position and tension of the sliding knot 81. In one example, the first and second lengths 75, 77 are tied into at least one half-hitch knot, which essentially "backs up" the sliding knot 81. Other types of locking knots come within the scope of this disclosure.

The result is a suture wrap cerclage 20, as substantially illustrated in FIG. 1, which supports a fractured bone under tension, and does so without implanting any metallic components into the body, and without requiring any structural changes (such as drilling or cutting) the bone 22. Further, the disclosed technique allows surgeons to provide the suture wrap cerclage efficiently and in a manner that is reliable and repeatable. While the method describes how to provide a single suture wrap cerclage 20, more severe fractures may require more than one suture wrap cerclage 20 provided along the length of the bone. In those instances, the benefits provided by this disclosure are even more apparent.

In the above-described method, the suture wrap cerclage is provided by tying at least one knot, and without implanting any structure in the body, with the exception of the suture 26. Other aspects of this disclosure, however, are "knotless," meaning the securing step includes securing the suture 26 to the bone 22 without tying any knots.

Figure 17:
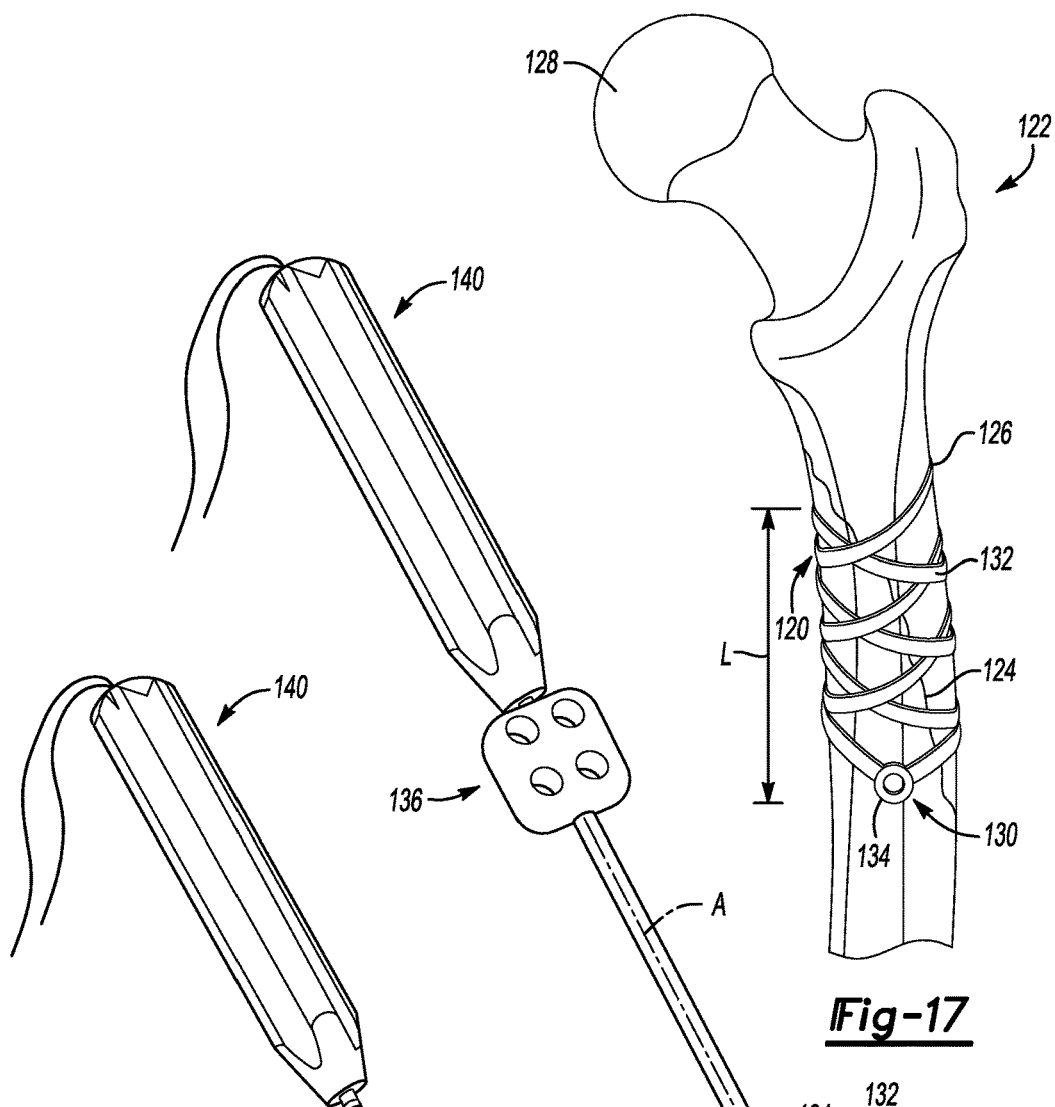
FIG. 17 illustrates a fractured bone having another example suture wrap cerclage.

One example knotless arrangement is shown in FIG. 17. In FIG. 17, a suture wrap cerclage 120 is provided around a bone 122, which in this example is a femur, having a fracture 124. The suture wrap cerclage 120 is first wrapped around the bone 122 at a first location 126, adjacent a head 128 of the bone 122, and travels along a length L of the bone to a second location 130, which is spaced-apart from the first location 126, adjacent the condyles of the bone 122, for example.

In the example of FIG. 17, the suture 132 providing the suture wrap cerclage 120 may be wrapped around the bone 122 using a suture passer similar to the suture passer 36 described above. The suture 132 is secured to bone at the second location 130 by a knotless suture anchor 134, using, for example, Arthrex's SwiveLock® or PushLock®.

Figure 18:
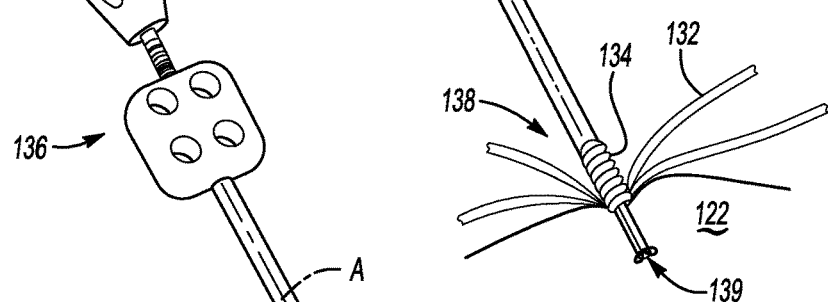
FIG. 18 illustrates an example inserter in a first position.
Figure 19:
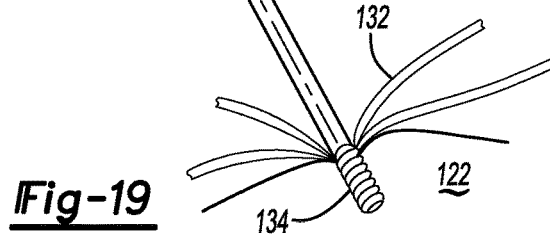
FIG. 19 illustrates an example inserter in a second position.

In general, the knotless suture anchor 134 is positioned by an inserter 136 (FIG. 18) including a distal end 138, a proximal end 140, and a longitudinal axis A between the distal end 138 and the proximal end 140. A first member including an eyelet 139 (such as an eyelet formed by a folded end of suture or a hard eyelet provided by an implant) is oriented to thread the suture 132 across the longitudinal axis A. Further, the first member is situated near the distal end 138 of the inserter and is configured to be placed in bone 122. A second member, which in one example is the anchor 134, is situated near the distal end 138 of the inserter 136. The second member 134 is moveable, by a portion of the inserter 136, relative to the first member in a distal direction toward the eyelet into a suture securing position where the second member 134 locks the suture 132 in place, as shown in FIG. 19. Again, while one example has been described, other knotless anchors come within the scope of this disclosure.

Figure 20:
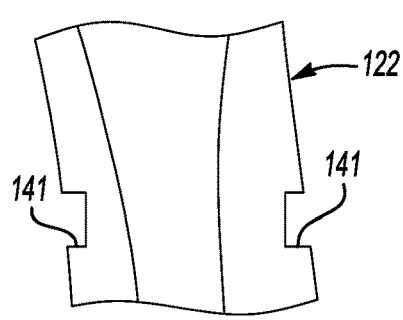
FIG. 20 illustrates a first example suture-retaining feature.
Figure 21:
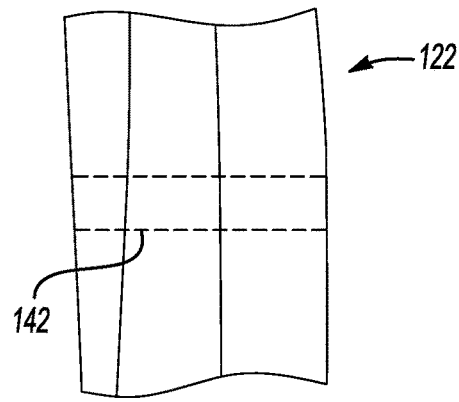
FIG. 21 illustrates a second example suture-retaining feature.

In some examples, the bone 122 may be machined to prevent slippage of the suture 132 from the first location 126 to the second location 130. In one example, illustrated in FIG. 20, the bone 122 may be provided with one or more notches 141 adjacent the first location 126, which are configured receive the suture 132. In another example, illustrated in FIG. 21, the bone 122 may be provided with a through-hole 142 (shown in phantom) adjacent the first location 126, through which the suture 132 may be fed. The notches 141 and through-hole 142 are only examples. Other types of suture-retaining features come within the scope of this disclosure. It should be understood that the suture-retaining features can be formed using conventional bone machining techniques, such as cutting or drilling.

Figure 22:
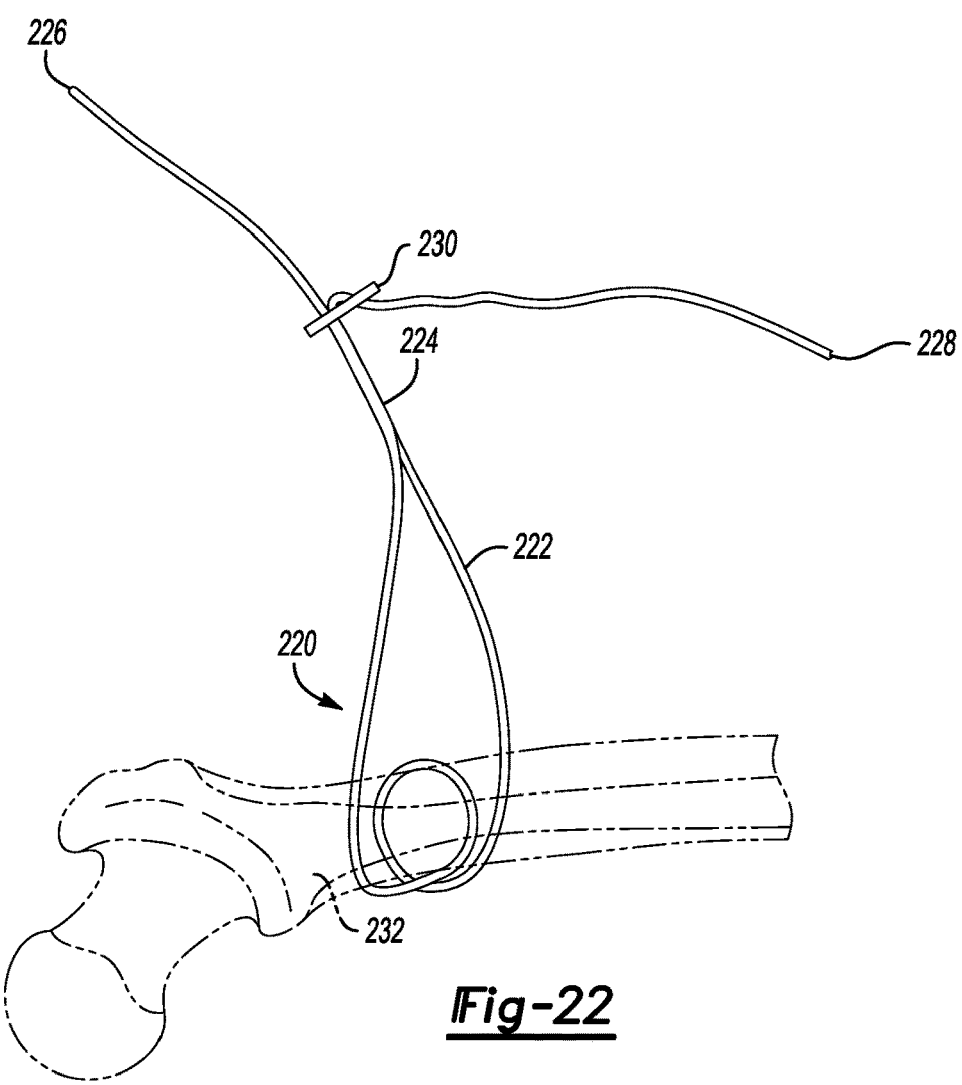
FIG. 22 illustrates a fractured bone having another example suture wrap cerclage.

FIG. 22 is another example securing technique that does not involve tying knots. In the example of FIG. 22, the suture wrap cerclage 220 is provided by a self-cinching suture 222 including at least one splice 224. An example type of self-cinching suture is included in Arthrex's TightRope®, which is a suture-button construct.

In general, the self-cinching suture 222 includes a first end 226, a second end 228, the splice 224, and a fixation device 230 (sometimes referred to as a "button"). In an example method, the second end 228 of the self-cinching suture is wrapped around a bone 232 one or more times (here, twice), and fed through the splice 224. In this example, the second end 228 is also fed through the fixation device 230. The second end 228 may be wrapped around the bone 232 using the above-discussed techniques.

Once wrapped, the second end 228 is pulled relative to the first end 226, which tightens the self-cinching suture 222 and cinches the suture 222 against the bone 232 to provide a suture wrap cerclage. Once tightened, the fixation device 230 maintains the position of the suture 222 relative to the bone 232. While one example self-cinching suture has been described, other types of self-cinching sutures come within the scope of this disclosure.

Figure 23:
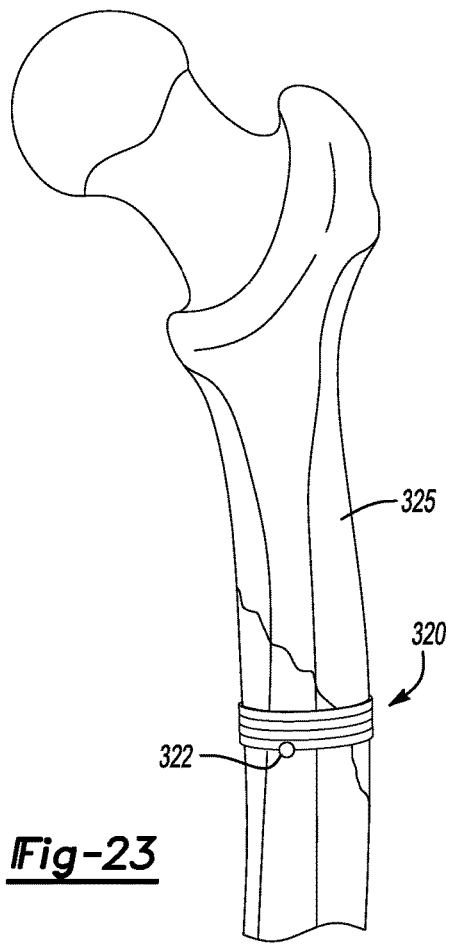
FIG. 23 illustrates a fractured bone having an example suture wrap cerclage, which is held in place using a bone screw.
Figure 24:
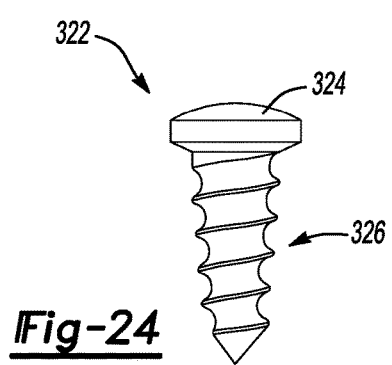
FIG. 24 illustrates the detail of an example bone screw.

FIGS. 23-24 illustrate yet another suture securing technique. In FIG. 23, a suture wrap cerclage 320 is held in place, at least in part, by a bone screw 322. An example bone screw 322 is illustrated in FIG. 24. As illustrated, the bone screw 322 includes a head 324 and a threaded shank 326. The head 324 in this example is sized to hold suture between the head 324 and bone 328. The bone screw 322 can be placed in a location adjacent an expected location of the suture wrap cerclage 320. In the illustrated example, the bone screw 322 is placed below an expected location of the suture wrap cerclage 320.

In FIG. 23, for example, the bone screw 322 is inserted partially into bone 328. Then, the suture providing the suture wrap cerclage 320 is wrapped about the bone per any of the above techniques. During wrapping, the bone screw 322 holds a position of the suture and prevents slippage of the suture. Once wrapped, the bone screw 322 can be tightened. When tightened, the bone screw 322—specifically the head 324—secures at least one length of suture to bone, which helps maintain the position of the suture warp cerclage 320.

Figure 25:
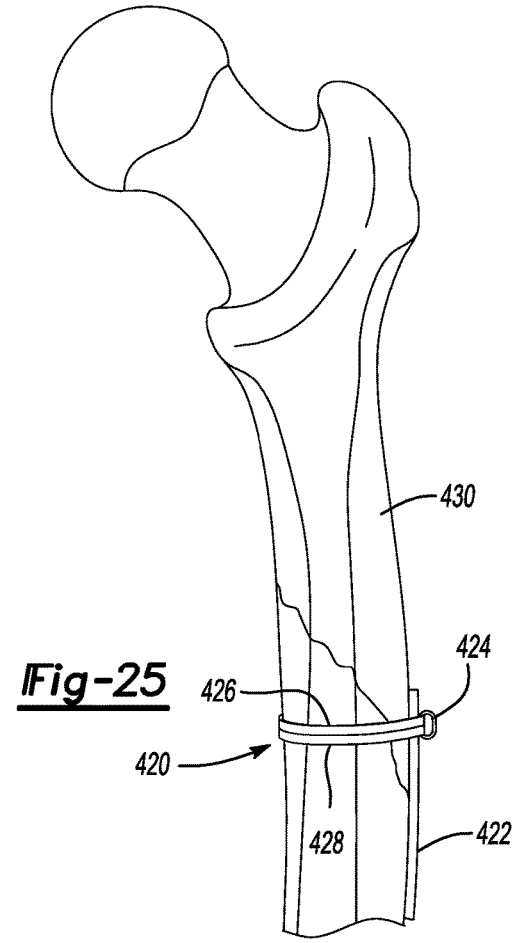
FIG. 25 illustrates a fractured bone having an example suture wrap cerclage, which is held in place using a bone plate.
Figure 26:
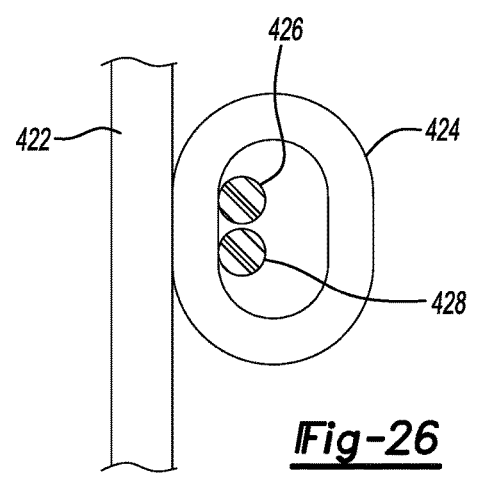
FIG. 26 illustrates an eyelet of the bone plate.

Another example suture wrap cerclage 420 is illustrated in FIGS. 25-26. In FIG. 26, the suture wrap cerclage 420 is provided relative to a bone plate 422 which includes an eyelet 424. The bone plate 422 may be fixed to the bone at one or more locations along its length. The eyelet 424, as perhaps best seen in FIG. 26, is fixed to the bone plate 422 and is configured to hold strands 426, 428 of suture in place relative to bone 430. The suture wrap cerclage 420 can be wrapped using any of the above techniques with the exception that, in this example, the strands 426, 428 pass through the eyelet. The eyelet 424 thus prevents slippage and substantially maintains a position of the suture wrap cerclage 420.

The suture wrap cerclages of this disclosure provide a reliable and effective bone cerclage, which promotes healing of fractured bones. Further, the disclosed methods and systems allow surgeons to provide suture wrap cerclages in an efficient manner without sacrificing consistency or quality.

It should be understood that terms such as "proximal" and "distal" are used consistent with their art-accepted meaning. These terms should not otherwise be considered limiting.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A method for providing a fractured bone with a bone cerclage, comprising:
    wrapping a folded piece of suture around a bone at least twice; and
    securing the suture to the bone.

2. The method as recited in claim 1, wherein the wrapping step comprises:
    wrapping the suture around the bone a first time by moving a folded end of the suture around the bone in a first direction; and
    wrapping the suture around the bone a second time by moving first and second free ends of the suture around the bone in a second direction opposite the first direction.

3. The method as recited in claim 2, wherein the folded end is pushed around the bone using a suture passer.

4. The method as recited in claim 3, wherein the first and second free ends are pulled around the bone by the suture passer after the folded end is pushed around the bone.

5. The method as recited in claim 3, wherein the securing step includes securing the suture to the bone by tying a knot.

6. The method as recited in claim 5, wherein the securing step includes providing a sliding knot between the folded end and the first and second free ends.

7. The method as recited in claim 6, wherein the sliding knot is partially pre-tied and includes an eyelet provided within a sheath.

8. The method as recited in claim 7, wherein the sheath includes at least one barb configured to resist removal of suture from the sheath.

9. The method as recited in claim 6, further comprising:
    tensioning the suture to tighten the wrapped suture relative to the bone.

10. The method as recited in claim 9, wherein the tensioning step includes using a tensioner to pull the first and second ends relative to the sliding knot to tighten the wrapped suture.

11. The method as recited in claim 1, wherein the securing step includes securing the suture to the bone without tying any knots.

12. The method as recited in claim 11, wherein the securing step includes anchoring the suture to the bone using a knotless anchor.

13. The method as recited in claim 12, wherein a portion of the suture providing a first wrap around the bone is secured to the bone by a suture-retaining feature formed in the bone.

14. The method as recited in claim 11, wherein the suture is a self-cinching suture including at least one splice, and the securing step includes pulling a portion of the self-cinching suture through the at least one splice to tension to the suture to the bone.

15. The method as recited in claim 1, wherein a bone screw maintains a position of the suture as the suture is wrapped around the bone, and the step of securing the suture to the bone includes tightening the suture against the bone using the bone screw.

16. The method as recited in claim 1, wherein the suture passes through an eyelet of a bone plate as the suture is wrapped around the bone.

17. The method as recited in claim 1, wherein the folded piece of suture is wrapped around an entirety of the bone at least twice.

* * * * *